United States Patent [19]

Kamatani et al.

[11] 4,028,185

[45] June 7, 1977

[54] METHOD FOR PRODUCING L(+)-TARTARIC ACID

[75] Inventors: Yoshio Kamatani, Osaka; Hisayoshi Okazaki, Kyoto; Ko Imai, Osaka; Noriaki Fujita, Suita; Yoshio Yamazaki, Toyonaka; Katsuhiko Ogino, Osaka, all of Japan

[73] Assignee: Takeda Chemical Ind., Ltd., Japan

[22] Filed: May 6, 1976

[21] Appl. No.: 683,802

[30] Foreign Application Priority Data

May 7, 1975  Japan ............................... 50-54956
May 7, 1975  Japan ............................... 50-54957
June 23, 1975  Japan ............................... 50-78124

[52] U.S. Cl. ................................. 195/30; 260/536

[51] Int. Cl.$^2$ .......................................... C12D 1/02
[58] Field of Search ..................................... 195/30

[56] References Cited

OTHER PUBLICATIONS

J. Bacteriology, vol. 70, pp. 405–414 (1955).

*Primary Examiner*—Alvin E. Tanenholtz
*Attorney, Agent, or Firm*—Wenderoth, Lind & Ponack

[57] ABSTRACT

Calcium cis-epoxysuccinate whose average particle size is not larger than 100 micron is converted into calcium L(+)-tartarate by a microorganism in a high concentration and in a better yield. This process is accelerated in the presence of a nonionic type surfactant of the medium.

6 Claims, No Drawings

METHOD FOR PRODUCING L(+)-TARTARIC ACID

This invention relates, in a process for producing tartaric acid by microbiologically hydrolyzing the epoxysuccinic acid, particularly to a method for producing L(+)-tartaric acid which comprises using, as the raw material, calcuium cis-epoxysuccinate whose average particle diameter is not larger than 100 micron, and having calcium L(+)-tartarate formed therewith.

The present inventors previously discovered a microorganism which is capable of producing L(+)-tartaric acid by microbiologically hydrolyzing cis-epoxysuccinic acid, and completed therefor the method qualified as consistently suitable for industrial manufacturing of L(+)-tartaric acid, and with which invention the present inventors filed on application for Japanese Patent Application Ser. Nos. 008149/75 and 013737/75. In the course of developing these methods, the present inventors have found out such a new fact that, upon using the calcium cis-epoxysuccinate as the raw material, the particle diameter of the crystal of said material has significant influence on the forming velocity as well as the yields of L(+)tartaric acid. Otherwise stated, in the case where the rate of forming is at low level, part of the once-formed tartaric acid tends to be decomposed, and hence it becomes difficult to gain the yields beyond a definite, stalemated rate. Therefore, in order that L(+)-tartaric acid is to be manufactured in a high concentration, in elevated yields, and in a relatively short period of time, the forming velocity of L(+)-tartaric acid constitutes an extremely important problem. The fact that the rate of forming is in a high level, in the actual working directly leads to the economically advantageous results to that extent. It is general knowledge that the forming velocity of L(+)-tartaric acid comes under the sway of such factors as the activity of the microorganisms used, culture medium, conditions of incubation, and various other phases. However, the effect of the particle size of the staring calcium cis-epoxy succinate has the high measure of importance among various factors mentioned above.

The concrete examples of this effect of said particle size are to be later illustrated in the preferred embodiments of this invention. In either of the cases illustrated in the embodiments, there is observed such a fact that, if the average particle diameter of the crystal of calcium cis-epoxysuccinate should exceed 100 micron, the forming velocity of L(+)-tartaric acid is conspicuously lowered, and also that the fermentation is retarded. Accordingly, that the average particle diameter of the crystals of calcium cis-epoxysuccinate amounts to no more than 100 micron, and that preferably 70 micron or less, is essentially and decisively advantageous for industrial production of L(+)-tartaric acid. The term "average particle diameter" as used herein refers to the average particle diameter by weight. What is preferable to be employed here as the qualified raw material is such a state or phase in which the particle diameter of "90% or more by weight" of the given particles is distributed in less than twice the average particle diameter.

As the second improvement to the method for producing L(+)-tartaric acid, the present inventors have found that upon using calcium cis-epoxysuccinate as the raw material, if nonionic type surfactant is present in the culture medium, the fermentation period is more remarkably curtailed, and the cacium cis-epoxysuccinate of high concentration can be converted into calcium L(+)-tartarate in a high efficiency.

Based on the above findings, research efforts have been further made, finally to culminate in the completion of the present invention.

Thus, the main object of the present invention is to provide an improved method for producing L(+)-tartaric acid in which the incubation of microorganism and the hydrolysis of calcium cis-epoxysuccinate into calcium L(+)-tartarate proceed simultaneously.

The second object of the present invention is to provide an improved method for producing L(+)-tartaric acid in which the hydrolysis of calcium cis-epoxysuccinate to calcium (+)-tartarate can be conducted in a high concentration of the material, in a better yield and in a shorter period.

Further objects will be explained in the following descriptions.

Thus, the present invention relates to an improved method for producing L(+)-tartaric acid or calcium salt thereof which comprises;

A. Preparing a culture medium containing calcium cis-epoxysuccinate of particle size not larger than 100 microns, B. Incubating in said culture medium a microorganism which is capable of hydrolyzing cis-epoxysuccinic acid to L(+)-tartaric acid, thereby converting said calcium cis-epoxysuccinate into calcium L(+)-tartarate.

A further improved feature of the method comprises (1) incorporating a nonionic type surfactant, in combination with said calcium cis-epoxysuccinate, in the culture medium; (2) incubating such a microorganism; and (3) thereby converting the calcium cis-epoxysuccinate into the calcium L(+)-tartarate.

As for the microorganisms to be employed in this invention, any sort of microbe is employable so long as it is capable of hydrolyzing cis-epoxysuccinic acid and of forming L(+)-tartaric acid. For example, the below itemized ones may be employed i.e., *Acinetobacter tartarogenes* KB-82 (IFO 13644; Ferm-P No. 2854; ATCC 31105); The same species KB-99 (IFO 13650; Ferm-P No. 2860; ATCC 31111); The same species KB-111 (IFO 13656; Ferm-P No. 2866; ATCC 31117); The same species KB112 (IFO 13657; Ferm-P No. 2867; ATCC 31118); *Agrobacterium aureum* KB-91 (IFO 13647; Ferm-P No. 2857; ATCC 31108); *Agrobacterium viscosum* KB-105 (IFO 13652; Ferm-P No. 2862; ATCC 31113); Rhizobium validum KB-97 (IFO 13648; Ferm-P No. 2858; ATCC 31109); The same species KB-106 (IFO 13653; Ferm-p No. 2863; ATCC 31114); *Pseudomonas species* KB-86 (IFO 13645; Ferm-P No. 2855; ATCC 31106).

The particulars of the bacteriological characteristics of these microbes are described below:

1. Taxonomic properties of the strains KB-82, KB-99, KB-111, and KB-112.
   a. Cell morphology.
      1. Spherical rods, 0.8–1.0 by 1.0–1.3 $\mu$m.
      2. In youg cultures short rod cells and large irregular cells are found. In older cultures the cells are nearly spherical.
      3. Non-motile.
      4. Non-sporing.
      5. Gram-negative.
      6. Non-acid-fastness.
   b. Cultural characteristics.

1. Nutrient agar plate: Circular, entire, convex, smooth, grayish white, opaque, glistening.
2. Agar slant: Growth moderate, filiform, smooth, grayish white, glistening.
3. Broth: Slightly turbid; no surface growth; sediment.
4. Gelatin stab: No liquefaction.
5. Litmus milk: Alkaline; no peptonization.

c. Physiological properties.
  1. Nitrate reduction: KB-111 and KB-112 are positive but KB-82 and KB-99 are negative in nitrate broth.
  2. Denitrification does not occur.
  3. Methyl red test: negative.
  4. Acetylmethylcarbinol is not produced.
  5. Indole is not produced.
  6. Hydrogen sulfide is not produced.
  7. Starch is not hydrolized.
  8. Citrate is utilized.
  9. Nitrates and ammonium salts are utilized as nitrogen sources.
  10. Achromogenic.
  11. Urease is produced.
  12. Oxidase: positive.
  13. Catalase: positive.
  14. No growth at pH 4.5 and 8.6. Optimal pH, at about 7. No growth at 8° C and 40° C. Optimal temperature, at about 30° C.
  15. Aerobic.
  16. High and Leifson test: oxidative.
  17. Acid but no gas from L-arabinose, D-xylose, and D-fructose. Slightly acid but no gas from D-glucose, D-mannose, D-galactose, and glycerol. No acid and no gas from maltose, lactose, trehalose, D-sorbitol, D-mannitol, inositol, and starch.

d. Other taxonomic properties.
  1. Resistant to 5 units of penicillin.
  2. Isolated from soil.

2. Taxonomic properties of the strain KB-86.

a. Cell morphology.
  1. Rods, 0.6–0.8 by 1.5–3.0 μm.
  2. Not pleomorphic.
  3. Motile by polar monotrichous flagellum.
  4. Non-sporing.
  5. Gram-negative.
  6. Non-acid-fastness.

b. Cultural characteristics.
  1. Nutrient agar plate: Circular, entire, convex, smooth, translucent, creamy white, glastening.
  2. Agar slant: Growth moderate, filiform, smooth, creamy white, glistening.
  3. Broth: Slightly turbid; no surface growth; sediment.
  4. Gelatin stab: No liquefaction.
  5. Litmus milk: Unchanged.

c. Physiological properties.
  1. Nitrates are not reduced in nitrate broth.
  2. Denitrification does not occur.
  3. Methyl red test is negative.
  4. Acetylmethylcarbinol is not produced.
  5. Indole is not produced.
  6. Hydrogen sulfide is not produced.
  7. Starch is not hydrolized.
  8. Citrate is utilized.
  9. Nitrates and ammonium salts are utilized as nitrogen sources.
  10. Water soluble pigments are not produced.
  11. Urease is produced.
  12. Oxidase: positive.
  13. Catalase: positive.
  14. No growth at pH 6.0 and 10.5. Optimal pH, at about 7. No growth at 40° C. Growth at 10° C. Optimal temperature, between 25° and 30° C.
  15. Aerobic.
  16. Hugh and Leifson test: oxidative,
  17. Acid but no gas from L-arabinose, D-xylose, D-glucose, D-mannose, D-fructose, D-galactose, maltose, sucrose, trehalose, D-sorbitol, D-mannitol, and glycerol. No acid and no gas from lactose, inositol, and starch.

d. Other taxonomic properties.
  1. Nitrogen fixation does not occur.
  2. Amino acids and vitamins are not necessary for growth.
  3. Isolated from soil.

3. Taxonomic properties of the strain KB-91.

a. Cell morphology.
  1. Rods, 0.5–0.7 by 1.0–3.0 μm.
  2. Not pleomorphic.
  3. Motile by one to three peritrichous flagella.
  4. Non-sporing.
  5. Gram-negative.
  6. Non-acid-fastness.

b. Cultural characteristics.
  1. Nutrient agar plate: Circular, spreading, convex, transparent, yellow, glistening.
  2. Agar slant: Growth moderate, spreading, smooth, yellow, glistening.
  3. Broth: Turbid; no surface growth; sediment.
  4. Gelatin stab: Stratiform liquefaction.
  5. Litmus milk: Neutral to slightly alkaline without serum zone.

No peptonization. Grayish brown color after 2 weeks.

c. Physiological properaties.
  1. Nitrates are not reduced in nitrate broth.
  2. Denitrification does not occur.
  3. Methyl red test negative.
  4. Acetylmethylcarbinol is not produced.
  5. Indole is not produced.
  6. Hydrogen sulfide is not produced.
  7. Starch is not hydrolized.
  8. Citrate is utilized.
  9. Nitrates and ammonium salts are utilized as nitrogen sources.
  10. Chromogenic.
  11. Urease is produced.
  12. Oxidase: positive.
  13. Catalase: positive.
  14. No growth at pH 4.5 and 10.5. Optimal pH, at about 7. No growth at 40° C. Growth at 10° C. Optimal temperature, at about 30° C.
  15. Aerobic.
  16. Hugh and Leifson test: oxidative.
  17. Acid but no gas from L-arabinose, D-glucose, D-mannose, D-fructose, D-galactose, lactose, trehalose, D-sorbitol, D-mannitol, inositol. No acid and no gas from D-xylose, maltose, sucrose, glycerol, and starch.

d. Other taxonomic properties.
  1. 3-Ketolactose production test: positive.
  2. Amino acids and vitamins are not necessary for growth.
  3. Growth on aniline blue glucose agar. Dye is not absorbed.

4. Cellulose is not decomposed.
5. Isolated from soil.
6. Not parasitic for plants as checked.
4. Taxonomic properties of the strain KB-105.
  a. Cell morphology.
    1. Rods, 0.5–0.7 by 1.0–3.0 μm.
    2. Not pleomorphic.
    3. Motile by one to three peritrichous flagella.
    4. Non-sporing.
    5. Gram-negative.
  b. Cultural characteristics.
    1. Nutrient agar plate: Circular, entire, convex, smooth, opaque, yellowish white, glistening.
    2. Agar slant: Growth moderate, filiform, yellowish white, glistening.
    3. Broth: Sediment, pellicle.
    4. Gelatin stab: No liquefaction.
    5. Litmus milk: Alkaline with serum zone.
  c. Physiological properties.
    1. Nitrates are not reduced in nitrate broth.
    2. Denitrification does not occur.
    3. Methyl red test: negative.
    4. Acetylmethylcarbinol is not produced.
    5. Indole is not produced.
    6. Hydrogen sulfide is not produced.
    7. Starch is not hydrolized.
    8. Citrate is utilized in Christensen's medium but not in Koser's medium.
    9. Nitrates and ammonium salts are utilized as nitrogen sources.
    10. Achromogenic.
    11. Urease is produced.
    12. Oxidase: positive.
    13. Catalase: positive.
    14. No growth at pH 4.5 and 10.5. Optimal pH, at about 7. No growth at 40° C. Growth at 10° C. Optimal temperature, at about 30° C.
    15. Aerobic.
    16. Hugh and Leifson test: oxidative.
    17. Acid but no gas from L-arabinose, D-xylose, D-glucose, D-mannose, D-fructose, D-galactose, maltose, sucrose, trehalose, D-sorbitol, D-mannitol, and glycerol. No acid and no gas from lactose, inositol, and starch.
  d. Other taxonomic properties.
    1. 3-Ketolactose production test: positive.
    2. Vitamin necessary for growth.
    3. Growth on aniline blue glucose agar. Dye is not absorbed.
    4. Viscous colonies are formed on sugar media.
    5. Cellulose is not decomposed.
    6. Isolated from soil.
    7. Not parasitic for plants as checked.
5. Taxonomic properties of the strains KB-97 and KB-106.
  a. Cell morphology.
    1. Short rods, 0.8–1.0 by 1.0–1.5 μm.
    2. In young cultures large irregular cells are found. In older cultures the cells become coccoid rods.
    3. Non-motile.
    4. Non-sporing.
    5. Gram-negative.
    6. Non-acid-fastness.
  b. Cultural characteristics.
    1. Nutrient agar plate: Circular, entire, convex, smooth, grayish white, opaque, glistening.
    2. Agar slant: Growth moderate, filiform, smooth, grayish white, glistening.
    3. Broth: Slightly turbid; no surface growth; sediment.
    4. Gelatin stab: No liquefaction.
    5. Litmus milk: Slightly alkaline; not peptonized; no serum zone.
  c. Physiological properties.
    1. Nitrate reduction: KB-106 is positive but KB-97 is negative in nitrate broth.
    2. Denitrification does not occur.
    3. Methyl red test: negative.
    4. Acetylmethylcarbinol is not produced.
    5. Indole is not produced.
    6. Hydrogen sulfide is not produced.
    7. Starch is not hydrolized.
    8. Citrate is not utilized.
    9. Nitrates and ammonium salts are utilized as nitrogen sources.
    10. Achromogenic.
    11. Urease is produced.
    12. Oxidase: positive.
    13. Catalase: positive.
    14. No growth at pH 4.5 and 8.6. Optimal pH, at about 7. No growth at 40° C. Growth at 10° C. Optimal temperature, at about 30° C.
    15. Aerobic.
    16. Hugh and Leifson test: oxidative.
    17. Acid but no gas from L-arabinose, and D-fructose. Slightly acid but no gas from D-xylose, D-glucose, D-mannose, D-galactose, and glycerol. No acid and no gas from maltose, sucrose, lactose, trehalose, D-sorbitol, D-mannitol, inositol, and starch.
  d. Other taxonomic properties.
    1. 3-Ketolactose is not produced.
    2. Growth on yeast extract media within 3 days.
    3. Isolated from root nodules of clover.

The method of the present invention is carried out by adding calcium cis-epoxysuccinate into the culture medium, in the course of microbe-incubation process, thereby making it possible to perform the simultaneous and paralleled actions of microbe-incubation and chemical reaction.

Upon practicing the incubation work for the microbes, the culture medium may be either in liquid state or solid state; but commonly applicable as well as more convenient way is to resort to shaking culture, or aerated agitation culture, which are based on the liquid culture medium.

There is no paeticular limitation or restrictive conditions in determining the state of the culture medium, that is, any sort of culture medium may be employed to the extent that the culture medium can accommodate said microbes, allowing them to grow up normally and securely, and also that the enzyme system which is capable of converting the calcium cis-epoxysuccinate into calcium L(+)-tartarate can be properly formed therein. For example, as the carbon source, calcium cis-epoxysuccinate, glucose, lactose, glycerin, sucrose (i.e., succharose), molasses, organic acids, hydrocarbons, and the like, may be used; and as the nitrogen source, there may be designated as examples such hydrolysate of protein as peptone, protein hydrolyzate, e.g. casamino acid (manufactured by Difco) and N-Z Amine (manufactured by Schefield), along with such substances as yeast extract, soy bean cakes, corn steep liquor, amino acids, various kinds of ammonium salts, various kinds of nitrates, and other organic, or inorganic nitrogen compounds, all of the above being validly applicable. Further, as the inorganic salts, various kinds of phosphates, magnesium sulfate, sodium chloride, and the like, may be added as the pertinent additives; and also, for the purpose of encouraging the growth of bacteria, various kinds of vitamins, compounds associated with nucleic acid, etc., may be added. Whatever incubating method may be adopted for the actual working occasions, it is recommendable to add, at the starting time of incubation or cultivating, cis-epoxysuccinate into the culture medium, even if in small amount, in that it is efficacious to yield better results.

Again, when setting out on the incubation work, it is preferable to inoculate the culture medium with some proper amount of culture broth which may be obtained through the pre-culturing which has been done beforehand on a small scale.

The incubating conditions, involving culturing temperature, duration of culturing time, acidity-alkalinity of liquids prevalent in the culture medium, and the like factors, are subject to variation according to the kind of microorganisms employed, or to the composition and elements of the culture medium. However, if only adequate selection and adjustment are done simply aiming at the ultimate target of maximum yields of said enzyme system, it would justify and suffice the objective of the work. In many cases of practice, good result can be obtained by making incubation under aerobic condition, at around 20°–40° C, and for 1–7 days, meanwhile maintaining culture medium at around pH 5–9.

As the starting raw material, calcium cis-epoxysuccinate may be in whichever state of normal salt, acid salt or the mixture of them; but in the case of employing the raw material which contains an acid salt, it is commonly a favored practive to neutralize beforehand by calcium chloride, calcium carbonate and the like. Such a converting process is also feasible that sodium cis-epoxysuccinate, potassium cis-epoxysuccinate and the like be added to the reaction mixture containing the calcium chloride or other calcium salts which are equimolar as compared to said succinates, thereby making it possible to convert the succinates to the corresponding calcium salts.

On the occasion when the raw material, i.e., calcium cis-epoxysuccinate is added to the culture medium in the course of incubating process, the addition is generally conducted either prior to the starting time of incubation, or at an adequate time during the incubation. In this instance, the said material is to be made into, for example, the form of crystals of calcium salt, or else, into the form of a suspension in a proper solvent such as water; and said crystals or suspension is to be added all at one time, or continuously ranging over a given period of time, or intermittently at regular intervals during the incubation period of the microorganism.

The total amount of calcium cis-epoxysuccinate employable during the incubation of microorganisms may be not less than 5 % (weight/volume) or further not less than 30 % and it is possible to raise the amount up to as high as 50 % (as free acid).

As the preferred embodiment of the present method a nonionic type surfactant is added into the culture medium to curtail the incubation period and to convert the calcium cis-epoxysuccinate to calcium L(+)-tartarate effectively.

As for the nonionic surfactant to be employed in the method of this invention, there are a wide range of applicable ones, which are effectively used, such as sorbitan fatty ester (e.g., sorbitan monooleate, sorbitan trioleate, and the like); polyoxyethylene sorbitan fatty ester (e.g., polyoxyethylene sorbitan monolaurate, polyoxyethylene sorbitan monooleate, and the like); polyoxyethylene sorbitol fatty ester (e.g., polyoxyethylene sorbitol monolaurate, and the like); polyoxyethylene fatty ester (e.g., polyoxyethylene stearate, polyoxyethylene laurate, and the like); polyoxyethylene higher alcohol ether (e.g., polyoxyethylene lauryl alcohol ether, polyoxyethylene oleyl alcohol ether); polyoxyethylene alkyl aryl ether (e.g., polyoxyethylene nonyl phenol ether, polyoxyethylene octyl phenol ether, and the like); glycerol fatty ester (e.g. glyceryl monostearate, and the like); alkylene glycol fatty ester (e.g., propylene glycol monostearate, and the like); polyoxypropylene polyoxyethylene alkyl ether (e.g., polyoxypropylene polyoxyethylene cetyl alcohol ether, and the like); polyoxyethylene alkyl phenol-formaldehyde condensation derivative (e.g., polyoxyethylene nonyl phenol-formaldehyde resin, polyoxyethylene octyl phenol-formaldehyde resin, and the like); polyoxyethylene alkyl amine or amide (e.g., polyoxyethylene oleyl amine, polyoxyethylene oleyl amide, and the like); polyoxyethylene lanolin derivative; polyoxyethylene lanolin alcohol derivative; polyoxyethylene sorbitol bees wax derivative; polyoxyethylene castor oil derivative; polyoxyethylene polyol; polyoxypropylene polyol; polyoxyethylene oxypropylene polyol (e.g., ethylene diamine polyoxypropylene oxyethylene tetraol, and the like); polyoxyethylene tetrahydrofurfuryl alcohol; polyoxypropylene fatty ester; or the likes.

In ordinary cases, the surface active agents are used within the concentration range of 0.05–5.0%, (weight/volume) and more preferably at around 0.05–2.0%. And, addition of the total amount of surface active agents may be effected all at one time before starting the incubation, or fractionally in the course of the incubation.

As have been described above, calcium L(+)-tartarate having been formed in the culture broth or in the reaction medium can be readily recovered by means of filtration or centrifugation.

The starting calcium cis-epoxysuccinate is prepared from maleic acid in the following manner.

Thus, an aqueous solution or aqueous suspension containing a calcium compound and maleic acid in a ratio of 0.4 to 0.6 gram-atom of calcium per mol of maleic acid is reacted with hydrogen peroxide in the presence of an epoxydizing catalyst and thereto an additional and sufficient amount of a calcium compound is added to make available a total of approximately, 1 gram-atom of calcium compound as calcium per mole of starting maleic acid at a temperature not exceeding 40 degrees centigrade, whereby calcium cis-epoxysuccinate is allowed to separate out as crystals having an average particle diameter not in excess of 100 micron.

As said maleic acid, whichever of maleic acid and maleic anhydride may be employed. As said calcium compound, use may be made of such compounds as calcium oxide, calcium hydroxide, calcium carbonate, calcium acetate, calcium nitrate, calcium formate and so forth.

The proportion of such calcium compound to be added per mole of maleic acid must lie within the range of 0.4 to 0.6 gram-atom as calcium. In the case where the amount of calcium is less than 0.4 gram-atom, it will be found that, if cis-epoxysuccinic acid is formed in the epoxidization reaction, the speed of formation is low and the product cis-epoxysuccinic acid is liable to undergo hydrolysis, both phenomena leading to a reduced final yield of calcium cis-epoxysuccinate. Moreover, the product will be contaminated with calcium DL-tartarate. This results in the disadvantage that when the resultant calcium cis-epoxysuccinate is microbially converted to L(+)-tartaric acid, the product is contaminated with DL-tartaric acid. Conversely, if the proportion of calcium is in excess of 0.6 gram-atom, calcium cis-epoxysuccinate will separate out in the epoxidization reaction but the crystalline particles thus obtained will have a large average diameter, thus failing to meet the object of obtaining crystals with small particle diameters.

The pH after the addition of said calcium compound is desirably lower than pH 4.

As said epoxidizing catalyst, use may be made of tungstic acid, molybdic acid, heteropoly-acids of tungsten or molybdenum, or salts of such acids. The catalysts obtainable by supporting any of such acids or salts on a carrier inert to the reaction may also be employed.

The amount of such catalyst is preferably within the range of 0.001 to 0.05 gram-atom and, for still better results, within the range of 0.002 to 0.02 gram-atom as tungsten or molybdenum per mole of maleic acid. For practical purposes, the optimum proportion may be selected according to the mole ratio of maleic acid to hydrogen peroxide, the reaction temperature and so forth.

The proper amount of hydrogen per mole of maleic acid is somewhere between 0.8 mole to 1.1 moles. The hydrogen peroxide may generally be used as an aqueous solution. While maleic acid will be almost completely epoxidized with a substantially equimolar amount of hydrogen peroxide relative to maleic acid, complete epoxidation may be accomplished by using hydrogen peroxide in slight excess over maleic acid. If the mole proportion of hydrogen peroxide is smaller than that of maleic acid, the mother liquor from the crystallization of calcium cis-epoxysuccinate by addition of a calcium compound following the epoxidation reaction will be contaminated with the calcium salt of unreacted maleic acid. However, since this mother liquor containing the calcium maleate and soluble catalyst may as such be recycled for use in the next reaction cycle, the carrying-over of unreacted calcium maleate is not a practical disadvantage.

The reaction temperature is not more than 70° C and, preferably, within the range of 40° and 60° C.

Increasing the amount of catalyst enables one to lower the reaction temperature and control the formation of undesirable reaction byproducts. Increasing the reaction temperature will hasten and enable one to reduce the amount of catalyst but, at temperatures beyond a limit, product cis-epoxysuccinic acid will undergo severe hydrolysis, giving rise to DL-tartaric acid and thus interfering with the possibility of producing calcium cis-epoxysuccinate in high purity.

Following the epoxidation reaction, the temperature of the reaction mixture is brought to 40° C or less and the aforementioned calcium compound is added so as to crystallize calcium cis-epoxysuccinate. As an alternative, following the epoxidation reaction, the reaction mixture is adjusted so that the amount of calcium compound will be 0.5 gram-atom per mole of maleic acid and, then, cooled. The resultant crystals are recovered and suspended again in a suitable solvent such as water. Then, at a temperature not exceeding 40° C, a further amount of calcium compound is added. The temperature at which the calcium compound is added has a significant influence upon the particle size of product calcium cis-epoxysuccinate. Thus, if the addition temperature is over 40° C, the particle size of product calcium cis-epoxysuccinate will be greater and it is only at temperatures not over 40° C that finely divided calcium cis-epoxysuccinate with an average particle diameter not in excess of 100 micron will be obtained. Below 40° C, the average particle size of calcium cis-epoxysuccinate can be decreased by lowering the temperature and, therefore, the temperature of adding the calcium compound may be preselected according to the desired particle diameter. The amount of calcium compound to be added at this stage is such that, taken together with the amount of calcium compound previously added for the epoxidation reaction, it will give a total of approximately 1 gram-atom as calcium per mole of the maleic acid employed. The pH of the reaction mixture after this addition of a calcium compound is preferably in the neighborhood of neutrality, for example between 5 and 9. Under such conditions the solubility in water of calcium cis-epoxysuccinate will be about 1 percent or less and, therefore, the substantially entire amount of calcium cis-epoxysuccinate will separate out as crystals.

From the reaction product mixture thus obtained, calcium cis-epoxysuccinate is recovered by filtration, centrifugation or the like and rinsed. By such procedures, there can be obtained fine particles of calcium cis-epoxysuccinate least contaminated with impurities such as calcium maleate, calcium DL-tartarate, catalyst, etc. Where the filtrate or mother liquor contains the soluble catalyst, the liquor can be reused for the next cycle of reaction. When the epoxidation reaction has been carried out with a solid catalyst, the catalyst may be separated by sieving or other suitable procedure after the epoxidation reaction or the formation of calcium cis-epoxysuccinate so that it may be reused as catalyst.

While the preferred embodiments of the method of this invention are shown in the following examples, it is to be construed that the following examples are described for illustrating purposes only, and it will be obvious that the methods particularly described in the following examples are not to be construed as limitations of the content of this invention.

EXAMPLE 1

Strains of such species as *Acinetobacter tartarogenes* KB-111, *Pseudomonas* species KB-86, *Agrobacterium aureum* KB-91, and *Rhizobium validum* KB-106 are respectively used to inoculate 30 ml of liquid culture medium, contained in Erlenmeyer flask of 200 ml-capacity, composed of corn steep liquor (0.2%), sodium nitrate (0.2%) dipotassium hydrogen phosphate (0.1%), magnesium sulfate (0.05%, and ferrous sulfate (0.001%), pH 7.0; and simultaneously, calcium cis-epoxysuccinate whose particles vary in average particle diameter one another is to be added in such way that the final concentration of said calcium salt may become 30% as the free acid; and after which the mixture is subjected to rotatory shake culture at 28° C for 2 days. The culture solution obtained from the above is then filtered to collect the crystals, and subsequently solubilized with sulfuric acid; and the resultant substance is centrifuged so as to eliminate the insoluble part. Finally the quantitative determination of L(+)-tartaric acid is carried out depending upon the optical rotation 436 mμ. The results of determination are shown in TABLE 1. In the TABLE, rates of yields of L(+)-tartaric acid are indicated in terms of molar yields; and with which 100% value represents the case where 1 mole of L(+)-tartaric acid has been formed from 1 mole of cis-epoxysuccinic acid.

TABLE 1

| Strain | Rate of Yields of L(+)-Tartaric Acid (%) Average Particle Diameters of Calcium Cis-Epoxysuccinate (μ) | | | | | | |
|---|---|---|---|---|---|---|---|
| | 200 | 170 | 130 | 100 | 80 | 70 | 50 |
| Acinetobacter tartarogenes KB-111 | 10 | 13 | 25 | 65 | 70 | 84 | 83 |
| Pseudomonas species KB-86 | 3 | 5 | 11 | 27 | 30 | 31 | 30 |
| Agrobacterium aureum KB-91 | 9 | 13 | 17 | 41 | 43 | 49 | 52 |
| Rhizobium validum KB-106 | 20 | 25 | 40 | 83 | 87 | 92 | 93 |

EXAMPLE 2

A strain of Acinetobacter tartarogenes KB-112 is used to inoculate 500 ml each of liquid culture media, contained in two Sakaguchi flasks of 2 l-capacity each, composed of glucose (0.5%) and corn steep liquor (1.0%), pH 7.0; and these cultures are subjected to reciprocating shake culture at 28° C for 24 hours, thereby obtaining 1l of culture solution. This culture solution is then transferred to a tank of 50 l-capacity which contains 30 l of liquid culture medium composed of casamino acid (0.05%), ammonium nitrate (0.1%), dipotassium hydrogen phosphate (0.2%), magnesium sulfate (0.05%), and ferrous sulfate (0.001%), pH 7.0; and at the same time, 9.0 kg. as the free acid of calcium cis-epoxysuccinate (average particle size: 50 micron) is added, the resultant mixture then being incubated at 30° C for 40 hours. Around 40 l of culture solution obtained from the above is filtered by means of the filterpress, and rinsed with water. After rinsing, the solid substance is suspended in 30 l of water, thoroughly agitated, and is thereafter left standing for a while to permit the solid substance to precipitate. Subsequent treatments are such that around 20 l of supernatant liquid is discarded, 20 l of water is again added, stirred well, and then filtered with the filter press. The crystals of calcium L(+)-tartarate finally obtained from the above comes up to 12.0 kg. (purity: 98%) as anhyride.

By way of contrasting with the above example, another experiment is given here, in which the strain of the same species, i.e., KB-112, is used. In this experiment, the incubation and reaction are carried out under the selfsame conditions as the preceding example, only except that the average particle diameter of calcium cis-epoxysuccinate, which is used as the raw material, is 130 micron. Around 40 l of the culture solution obtained from the above incubation is purified by quite the same method as mentioned above. In the crystals recovered from the above purification, the residue of cis-epoxysuccinic acid is confirmed to actually exist; and therefore, the content of L(+)-tartaric acid is measured as the quantitative determination by use of the method of Example 1; and by utilizing the result of said determination, the rate of yields of calcium L(+)-tartarate is figured out. As the consequence, it is found out that the yield of calcium L(+)-tartarate is equivalent to 7.8 kg. as the anhyride.

Similarly, use is made of such strains as Acinetobacter tartarogenes KB-82, Agrobacterium viscosum KB-105, Rhizobium validum KB-97 and Acinetobacter tartarogenes KB-99, and good results are attained (average particle size of calcium cis-epoxysuccinate: 50 micron)

EXAMPLE 3

Acinetobacter tartarogenes KB-112 are used to inoculate 30 ml of culture medium, contained in the Erlenmeyer flask of 200 ml-capacity, which culture medium having been set up into such constitution that, to the basic culture medium which is composed of casamino acid (0.05%), ammonium nitrate (0.1%), dipotassium hydrogen phosphate (0.2%), magnesium sulfate (0.05%), ferrous sulfate (0.001%), pH 7.0, various sorts of nonionic surfactants are added so that the respective kinds of surface active agents may come to the concentration of 0.1%. And simultaneously, the crystals of calcium cis-epoxysuccinate (average particle size: 60 micron) is added, in such way that it may come to the final concentration of 40% counted as the free acid; and the above mixture is subjected to rotatory shake culture at 30° C, and for 2 days, and thence being allowed to exert reaction effect. After the termination of reaction, and the crystals are collected by filtration and, after addition of sulfuric acid, subjected to centrifugal separator to eliminate the solid substances. Subsequently, the quantitative determinations are made, with respect to L(+)-tartaric acid, by depending upon the optical rotation at 436 mμ; and with respect to the remaining cis-epoxysuccinic acid, by using Payne & Williams Method (G. B. Payne and P. H. Williams: Journal of Organic Chemistry, 24, 54, (1959)). The results of determination turned out are shown in Table 3.

TABLE 3

| Description[1] Surface Active Agents | Mole Yields (%)[2] of L(+)-tartaric acid | Rate of Residues[3] (%) of cis-epoxy-succinic acid |
|---|---|---|
| NIKKOL SR-10 | 45 | 52 |
| NIKKOL TO-10 | 72 | 25 |
| NIKKOL GS-6 | 50 | 48 |
| NIKKOL MYS-10 | 47 | 50 |
| NIKKOL BC-7 | 52 | 43 |
| NIKKOL NP-18TX | 55 | 40 |
| NIKKOL MGS-C | 48 | 47 |
| NIKKOL PMS-SE | 46 | 50 |
| NIKKOL TW-20 | 75 | 21 |
| NIKKOL BWA-20 | 74 | 21 |
| NIKKOL HCO-50 | 73 | 23 |
| NIKKOL R-1020 | 73 | 21 |
| NIKKOL TF-4 | 54 | 42 |
| NIKKOL TPMS-30 | 70 | 26 |
| TETRONIC T-702 | 52 | 45 |
| Not Added | 34 | 64 |

LEGEND

[1]The components of the Surface Active Agents used are as follows:
SR-10 : Sorbitan monooleate
TO-10 : Polyoxyethylene sorbitan monooleate
GS-6 : Polyoxyethylene sorbitol hexastearate
MYS-10 : Polyoxyethylene stearate
BC-7 : Polyoxyethylene cetyl alcohol ether
NP-18TX : Polyoxyethylene nonyl phenol ether
MGS-C : Glyceryl monostearate
PMS-SE : Propyleneglycol monostearate
TW-20 : Polyoxyethylene lanolin derivative
BWA-20 : Polyoxyethylene lanolin alcohol derivative
HCO-50 : Polyoxyethylene hardened castor oil derivative
R-1020 : Polyoxyethylene nonyl phenolformaldehyde resin
TF-4 : Polyoxyethylene tetrahydrofurfuryl alcohol

TABLE 3-continued

TPMS-30 : Polyoxyethylene oxypropylene stearate
All the above are the products manufactured by NIKKO CHEMICALS CO., LTD.
TETRONIC T 702: Ethylenediamine poly(oxypropylene oxyethylene)tetraol (the product manufactured by ASAHI DENKA KOGYO CO.)
(= [2])Figures represents the conversion rate to L(+)-tartaric acid from cis-epoxysuccinic acid.
(= [3])Rate of residues of the cis-epoxysuccinic acid, Figures represent % residues with a residue of 12 g as free acid being taken as 100 %.

EXAMPLE 4

Acinetobacter tartarogenes KB-82, Pseudomonas species KB-86, Agrobacterium aureum KB-91, Acinetobacter tartarogenes KB-99, Agrobacterium viscosum KB-105, and Rhizobium validum KB-106, are respectively used to inoculate 50 ml of liquid culture medium, contained in the Erlenmeyer flask of 200 ml-capacity, composed of corn steep liquor (0.2 %), glucose (0.1 %), ammonium nitrate (0.1 %), dipotassium hydrogen phosphate (0.2 %), magnesium sulfate (0.05 %) and ferrous sulfate (0.001 %), pH 7.0; and simultaneously, calcium cis-epoxysuccinate (Average Particle size, 60 micron) is added in such way that its final concentration may become 30 % as the free acid, and thus the incubation is initiated. As described in TABLE 4, various classes of surfactants are added; and the mixture is subjected to shake culture at 30° C for 42 hours. From the result of cultivating, such a fact is observed that, with respect to each of the strains, the yield rates of L(+)-tartaric acid respectively show increased values as compared to the cases where just similar incubation is carried out without adding the surface active agent at all.

TABLE 4

| Strains | Concentration (%)* [1] of Surfactants when added | Time of Addition (h) | Mole Yield Rate (%) of L(+)-tartaric acid |
|---|---|---|---|
| Acinetobacter tartarogenes KB-82 | NONION LT-221 (0.2) | 0 | 83 |
|  | Not Added | — | 59 |
| Pseudomonas species KB-86 | NONION E-215 (0.05) | 0 | 47 |
|  | Not added | — | 31 |
| Agrobacterium aureum KB-91 | NONION L-4 (0.1) | 12 | 65 |
|  | Not Added | — | 50 |
| Acinetobacter tartarogenes | NIKKOL R-2030 (0.1) | 18 | 89 |
| KB-99 | Not Added | — | 77 |
| Agrobacterium viscosum | NIKKOL CO-60TX (0.05) | 0 | 59 |
| KB-105*(2) | Not Added | — | 48 |
| Rhizobium validum | PULRONIC L-61 (0.15) | 0 | 92 |
| KB-106 | Not Added | — | 85 |

LEGEND:
* [1]NINION LT-221 (Polyoxyethylene sorbitan monolaurate);
NONION E-215 (Polyoxyethylene oleyl ether);
NONION L-4 (Polyethylene glycol monolaurate).
[All of the above three are the products manufactured by NIPPON YUSHI CO. (Japan Fats & Oils Mfg. Co., Ltd.).]
NIKKOL R-2030 (Polyoxyethylene octyl phenolformaldehyde resin);
NIKKOL CO-60TX (Polyoxyethylene castor oil derivative);
The above two are the products manufactured by NIKKO CHEMICALS CO., LTD.
PULRONIC L-61 (Polyoxyethylene oxypropylene polyol)
[This is the product manufactured by ASAHI DENKA CO., LTD.]
* [2]In the case of this strain being incubated, 100 µg/ml of pyridoxal hydrochloride is added to the culture medium.

EXAMPLE 5

Rhizobium validum KB-97 and Acinetobacter tartarogenes KB-111, are used to inoculate respectively 500 ml of culture medium, contained in Sakaguchi flask of 2 l-capacity, of such constitution that the surfactant is added to the basic culture medium which is just the same as the one in Example 3; and simultaneously, calcium cis-epoxysuccinate (Average particle size: 70 micron) is added to the above in such way that its final concentration may become 50 % as the free acid. Subsequently, the above mixture is subjected to reciprocating shake culture at 28° C. The quantity of cis-epoxysuccinic acid left over as residue in the culture broth is followed by means of the thin-layer chromatography (Thin-layer: fine-crystal cellulose spot film, as manufactured by TOKYO KASEI Co.; Solvent: isopropyl ether-tetrahydrofuranformic acid-water (10:10:5:4); Color development: Brom-Cresol Green.)); and following the above, the incubation is continued until cis-epoxysuccinic acid disappears. Time elapsed during the converting reaction up until the endpoint of the reaction, along with the rate of yield of L(+)-tartaric acid forming (which is in molar yield figured out by the method used in Example 3), are indicated on TABLE 5, in which can be observed the curtailment of the reaction time and the increment in yield rate.

TABLE 5

| Strains | NONION OT-221* (0.15%) | | RIPONOX NCG* (0.1%) | | NIKKOL HCO-80* (0.2%) | | Not Added | |
|---|---|---|---|---|---|---|---|---|
|  | Time consumed (h) | Yield Rate (%) | Time consumed (h) | Yield Rate (%) | Time consumed (h) | Yield Rate (%) | Time consumed (h) | Yield Rate (%) |
| Rhizobium validum KB-97 | 84 | 89 | 96 | 89 | 78 | 92 | 108 | 85 |
| Acinetobacter tartarogenes KB-111 | 84 | 90 | 108 | 85 | 90 | 87 | 120 | 83 |

LEGEND:*
NONION OT-221: Polyoxyethylene sorbitan monooleate (manufactured by NIPPON YUSHI CO.-Japan Fats & Oils Mfg. Co.);
RIPONOX NCG: Polyoxyethylene alkyl phenol ether (manufactured by LION FATS & OILS MFG. CO.);

TABLE 5-continued

| Strains | NONION OT-221* (0.15%) | | RIPONOX NCG* (0.1%) | | NIKKOL HCO-80* (0.2%) | | Not Added | |
|---|---|---|---|---|---|---|---|---|
| | Time consumed (h) | Yield Rate (%) | Time consumed (h) | Yield Rate (%) | Time consumed (h) | Yield Rate (%) | Time consumed (h) | Yield Rate (%) |

NIKKOL HCO-80: Polyoxyethylene hardened castor oil derivative (manufactured by NIKKO CHEMICALS CO.).

EXAMPLE 6

Rhizobium validum KB-97 is used to inoculate 500 ml each of liquid culture medium contained in two Sakaguchi flasks of 2 l-capacity and composed of glucose (0.5 %), corn steep liquor (1.0 %), pH 7.0; and then subjected to reciprocating shake culture at 28° C, and for 24 hours, thereby obtaining around 1 l of the culture broth. This culture broth is transferred to a tank of 50 l-capacity which contains 30 l of liquid culture medium composed of corn steep liquor (0.2 %), ammonium nitrate (0.1 %), dipotassium hydrogen phosphate (0.2 %), magnesium sulfate (0.05 %), ferrous sulfate (0.001 %), and NIKKOL TW-20(0.1 %), pH 7.0; and at the same time, 6 kg. of calcium cis-epoxysuccinate (Average Particle size: 55 micron) is added counted as the free acid; and the resultant mixture is subjected to incubation at 30° C. After 19 hours has elapsed down from the starting time of incubation, 6 kg. of calcium cis-epoxysuccinate is further added counted as the free acid; and the mixture is placed under continued incubation up to a point of totalled 48 solid hours down from the starting of the incubation. Subsequent series of treatments are such that around 40 l of the obtained culture broth is filtered by means of the filter press; the solid part is rinsed with water; and is suspended in 30 l of water, which suspension is agitated thoroughly, after marking time to await precipitation of solid part, 20 l of supernatant part is discarded; 20 l of water is again added and stirred well; and the result is filtered with filter press, thus finally obtaining the crystals of calcium L(+)-tartarate. The quantity of this crystals is 15.9 kg.(purity: 98 %) as anhydride.

By way of contrasting with the above example, another experiment is conducted with, the same strain KB-97. In this experiment, the cultivation and reaction are carried out under the self-same terms and conditions as the preceding example, only except that NIKKOL TW-20 (surfactant) alone is eliminated from the culture medium used in the preceding example. Around 40 l of the culture broth which is obtained from the above is purified by quite the same method as above. In the crystals obtained through the above purification, the residue of calcium cis-epoxysuccinate is confirmed to actually exist when tested by means of the thin-layer chromatography (carried out in compliance with the method used in Example 5); and therefore, the content of L(+)-tartaric acid is subjected to quantitative determination by the method of Example 3. As the result, it is found that the quantity of yield of the calcium L(+)-tartarate is equivalent to 12.3 kg. as the anhydride.

EXAMPLE 7

Rhizobium validum KB-97 is used to inoculate 500 ml of a liquid culture medium (pH 7.0) contained in 2 l-capacity Sakaguchi flask composed of corn steep liquor (2.0 %), glucose (0.5 %) and this liquid culture is incubated at 28° C, for 24 hours, under reciprocating-shake culture. Thus obtained culture broth is transferred to a tank of 50 l-capacity which contains 30 l of the culture medium just self-same in composition as the one described above and the liquid culture medium in the said tank is subjected to incubation at 28° C for 24 hours under aerated agitation culturing. Around 15 l of the culture broth obtained therefrom is transferred into a tank of 200 l-capacity which contains 100 l of a liquid culture medium composed of corn steep liquor (0.5 %), ammonium nitrate (0.1 %), sodium dihydrogen phosphate (0.2 %), magnesium sulfate (0.05 %), ferrous sulfate (0.001 %), polyoxyethylene lanolin derivative (0.1 %) (pH 7.0) and simultaneously 40 kg of calcium cis-epoxysuccinate (Average particle size: 50 micron)(as free acid) is added.

The whole is subjected to aerated agitation culturing at 30° C for 30 hours. The resultant cultured broth and the washing water of the tank, about 150 l in total are subjected to Decantor type centrifuge (Sumitomo Heavy Industries, Ltd. TS-210F type) to separate calcium L(+)-tartarate as crystals. The crystals are suspended in about 100 l of water. After sufficiently stirring, the crystals are separated by said decantor type centrifuge and again suspended in about 70 l of water and stirred well. The suspension is subjected to a filter-press to give 54 kg of calcium L(+)-tartarate (purity 98%) as anhydride.

EXAMPLE 8

In 400 ml of water is dissolved 98 g of maleic anhydride. Then, 6.6 g of sodium tungstate (dihydrate) and 50 g of calcium carbonate (0.5 gram-atom as calcium per mole of maleic acid) are added and dissolved. The reaction temperature being maintained at 30° C, 102 g of a 35 % aqueous solution of hydrogen peroxide is added dropwise over a period of 1 hour. Following the dropwise addition, the reaction is further allowed to proceed for 7 hours. At a temperature of 30° C, with 50 g of calcium carbonate being gradually added, the reaction mixture is stirred until no more carbon dioxide gas evolves. The resultant crystals are recovered by filtration, rinsed with water and dried. The procedure provides 248 g (purity 99.5%) of calcium cis-epoxysuccinate (pentahydrate).

The average particle diameter of these crystals is found to be 72 $\mu$.

EXAMPLE 9

In 300 ml of water is dissolved 49 g of maleic anhydride. Then, 2.4 g of sodium molybdate (dihydrate) and 20.3 g of calcium hydroxide (0.55 gram-atom as calcium per mole of maleic acid) are added and dissolved.

Following the dropwise addition of 51 g of a 35 % aqueous solution of hydrogen peroxide at 50° C, the reaction is further conducted at 50° C for 5 hours.

Thereafter, the reaction mixture is cooled to 30° C and while this temperature is maintained, 16.7 g of calcium hydroxide (0.45 gram-atom as calcium per mole of maleic acid) is gradually added.

The mixture is stirred for 1 hour, after which the crystals are recovered by filtration. The procedure yields 112 g (purity 98 %) of calcium cis-epoxysuccinate (pentahydrate). The average particle diameter of these crystals is 38 $\mu$.

EXAMPLE 10

In 500 ml of water is dissolved 98 g of maleic anhydride, followed by the addition of 1.3 g of sodium tungstate (dihydrate) and the amount of calcium carbonate indicated in the table below. At a reaction temperature of 50° C, 97.2 g of a 35 % aqueous solution of hydrogen peroxide is added dropwise and the reaction is further carried out at 50° C. With the reaction mixture being maintained at 20° C, calcium carbonate is further added in a sufficient amount to make a total of 100 g taken together with the amount added for epoxidation (to make one gram-atom as calcium per mole of maleic acid), with stirring until the evolution of carbon dioxide gas ceases. The resultant crystals are collected by filtration. The results are set forth below in the table.

| $CaCO_3$ (g) as added for epoxidation | 30 | 40 | 50 | 60 | 70 |
|---|---|---|---|---|---|
| Number of gram-atoms as calcium | 0.3 | 0.4 | 0.5 | 0.6 | 0.7 |
| pH of maleic acid suspension | 1.3 | 1.5 | 2.9 | 3.4 | 3.6 |
| Reaction time (Hr) | 9 | 7 | 6 | 5 | 4 |
| Yield of calcium cis-epoxysuccinate (pentahydrate) (gramm) | 236 | 244 | 249 | 247 | 245 |
| Purity (%) of calcium cis-epoxysuccinate (pentahydrate) | 95 | 98 | 99 | 99 | 99 |
| Average particle diameter ($\mu$) of calcium cis-epoxysuccinate (pentahydrate) | 60 | 58 | 52 | 98 | 140 |

EXAMPLE 11

In 400 ml of water is dissolved 98 g of maleic anhydride. Then, 0.66 g of sodium tungstate (dihydrate) and 37 g of calcium hydroxide (0.5 gram-atom as calcium per mole of maleic acid) are added and dissolved.

At a reaction temperature of 60° C, 51 g of a 60 % aqueous solution of hydrogen peroxide is added dropwise, followed by reacting further at 60° C for 3 hours. The reaction mixture is cooled and at the temperature indicated below in the table, 50 g of calcium carbonate (0.5 gram-atom as calcium per mole of maleic acid) is gradually added. The mixture is stirred until the evolution of carbon dioxide gas ceases. Then, at a temperature of 20° C, the stirring is further continued for 1 hour and the resultant crystals are recovered by filtration. The results are set forth below in the table.

| Temperature (° C) at which $CaCO_3$ is added | 10 | 20 | 30 | 40 | 50 |
|---|---|---|---|---|---|
| Yield (g) of calcium cis-expoxysuccinate (pentahydrate) | 228 | 227 | 225 | 226 | 224 |
| Purity (%) of calcium cis-epoxysuccinate (pentahydrate) | 99 | 99 | 99 | 99 | 99 |
| Average particle diameter ($\mu$) of calcium cis-epoxysuccinate (pentahydrate) | 47 | 52 | 70 | 93 | 130 |

EXAMPLE 12

In 300 ml of water is dissolved 98 g of maleic anhydride. Then, 1.3 g of sodium tungstate (dihydrate) and 60 g of calcium carbonate (0.6 gram-atom as calcium per mole of maleic acid) are added.

At a reaction temperature of 60° C, 98 g of a 35 % aqueous solution of hydrogen peroxide is added dropwise, followed by reacting further at 60° C for 4 hours. The reaction mixture is cooled and the resulting crystals are collected by filtration. The crystals are suspended in 300 ml of water. At 10° C 40 g of calcium carbonate (0.4 gram-atom per mole maleic acid) is gradually added thereto and the slurry is stirred until the evolution of carbon dioxide gas ceases. The resultant crystals are recovered by filtration as 244 g of calcium cis-epoxysuccinate 5 hydrate (purity 99 %). The average diameter of the crystals is 75 micron.

What we claim is:

1. In a method for producing L(+)-tartaric acid or calcium salts thereof by microbiologically hydrolyzing epoxy-succinic acid or calcium salts thereof, the improvement of which comprises;
   A. preparing a culture medium containing calcium cis-epoxysuccinate of particle size not larger than 100 microns,
   B. incubating in said culture medium a microorganism which is capable of hydrolyzing cis-epoxysuccinic acid to L(+)-tartaric acid, thereby converting said calcium cis-epoxysuccinate into calcium L(+)-tartarate.

2. A method according to claim 1, wherein said starting calcium cis-epoxysuccinate is prepared by (1) reacting an aqueous solution or aqueous suspension containing maleic acid and a calcium compound in a ratio of 0.4 to 0.6 gram-atom as calcium to each mole of maleic acid with hydrogen peroxide in the presence of an epoxidizing catalyst, (2) then adding an additional amount of a calcium compound at a temperature not over 40° C to make available a total of approximately one gram-atom as calcium per mole of starting material maleic acid, and (3) thereby causing calcium cis-epoxysuccinate to separate out as crystals.

3. A method according to claim 2, wherein said epoxydizing catalyst is one selected from tungstic acid, molybdic acid, heteropoly-acid of tungsten or molybdenum and salts of them.

4. A method according to claim 1, wherein a nonionic type surfactant is incorporated in the culture medium.

5. A method according to claim 4, wherein the nonionic type surfactant is one selected from the group consisting of sorbitan fatty ester, polyoxyethylene sorbitan fatty ester, polyoxyethylene sorbitol fatty ester, polyoxyethylene fatty ester, polyoxyethylene higher alcohol ether, polyoxyethylene alkyl aryl ether, glycerol fatty ester, alkylene glycol fatty ester, polyoxypropylene polyoxyethylene alkyl ether, polyoxyethylene alkyl phenolformaldehyde condensation derivative, polyoxyethylene alkyl amine or amide, polyoxyethylene lanolin derivative, polyoxyethylene lanolin alcohol derivative, polyoxyethylene sorbitol bees wax derivative, polyoxyethylene castor oil derivative, polyoxyethylene polyol, polyoxypropylene polyol, polyoxyethylene oxypropylene polyol, polyoxyethylene tetrahydrofurfuryl alcohol and polyoxypropylene fatty ester.

6. A method according to claim 4, wherein the concentration of nonionic type surfactant is 0.05–5.0 % (weight per volume).

* * * * *